(12) United States Patent
Kim et al.

(10) Patent No.: US 7,763,730 B2
(45) Date of Patent: Jul. 27, 2010

(54) METHOD PREPARATION CLOPIDOGREL AND INTERMEDIATES USED THEREIN

(75) Inventors: Eun Sook Kim, Seoul (KR); Hee Cheol Kim, Yongin-si (KR); Bo Sung Kwon, Yongin-si (KR); Sangmin Yun, Seongnam-si (KR); Mi Young Ko, Suwon-si (KR); Cheol Kyung Kim, Suwon-si (KR); Kwee Hyun Suh, Suwon-si (KR)

(73) Assignee: Hanmi Pharm. Co., Ltd, Kyungki-do (KR)

( * ) Notice: Subject to any disclaimer, the term of this patent is extended or adjusted under 35 U.S.C. 154(b) by 0 days.

(21) Appl. No.: 12/549,850

(22) Filed: Aug. 28, 2009

(65) Prior Publication Data

US 2009/0318701 A1    Dec. 24, 2009

Related U.S. Application Data

(62) Division of application No. 11/917,794, filed as application No. PCT/KR2005/004017 on Nov. 28, 2005, now Pat. No. 7,652,140.

(30) Foreign Application Priority Data

Jun. 23, 2005    (KR) .................... 10-2005-0054303

(51) Int. Cl.
*C07D 495/04* (2006.01)
(52) U.S. Cl. ..................................... 546/114
(58) Field of Classification Search ................. 546/114
See application file for complete search history.

(56) References Cited

U.S. PATENT DOCUMENTS

2005/0059696 A1    3/2005    Reddy et al.

FOREIGN PATENT DOCUMENTS

| WO | 0061549 A2 | 10/2000 |
| WO | 02059128 A2 | 8/2002 |
| WO | 03004502 A1 | 1/2003 |

*Primary Examiner*—Patricia L Morris
(74) *Attorney, Agent, or Firm*—Sughrue Mion, PLLC

(57) ABSTRACT

Optically pure clopidogrel can be prepared in a high yield by optically resolving a racemic form of the compound of formula (II) using an optically active amine to form the optically active form of the compound of formula (III) or its acid-addition salt; and methylating the compound of formula (III) or its acid-addition salt.

4 Claims, No Drawings

METHOD PREPARATION CLOPIDOGREL AND INTERMEDIATES USED THEREIN

CROSS-REFERENCE

This is a divisional of application Ser. No. 11/917,794, filed Dec. 17, 2007, now U.S. Pat. No. 7,652,140, which is a National Stage 371 of PCT/KR2005/004017 filed Nov. 28, 2005 which claims benefit from Korean Patent Application 10-2005-0054303 filed Jun. 23, 2005 all of which are incorporated herein by reference.

FIELD OF THE INVENTION

The present invention relates to a method of preparing optically pure clopidogrel in a high yield and a novel intermediate used therein.

BACKGROUND OF THE INVENTION

Clopidogrel, methyl (S)-(+)-α-(2-chlorophenyl)-6,7-dihydrothieno[3,2-a]pyridine-5(4H)-acetate of formula (I), is a platelet-aggregation inhibitor which is effective in treating peripheral arterial diseases such as stroke, thrombosis and embolism, as well as coronary arterial diseases such as myocardial infarction and angina pectoris:

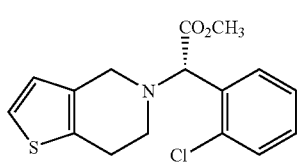
(I)

Various methods of preparing clopidogrel are described in European Patent Nos. 0,281,459, 0,466,569, 0,971,915, 0,099,802, 1,021,449, 1,404,681 and 1,353,928, and International Publication Patent No. WO 2004/094374. Among these methods, preferred in terms of commercial applicability are methods which involve resolving a racemate composed of clopidogrel of formula (I) or an intermediate thereof and its levorotatory isomer using an optical resolution agent.

For example, European Patent No. 0,281,459 discloses a method of preparing clopidogrel of formula (I) by way of reacting a racemate of clopidogrel with (1R)-(−)-10-camphorsulfonic acid to selectively form camphorsulfonate of clopidogrel, and removing the camphorsulfonate moiety therefrom (optical resolution process); and European Patent Nos. 0,099,802 and 1,353,928, by way of optically resolving an intermediate of clopidogrel racemate as described above using (1R)-(−)-10-camphorsulfonic acid, and then preparing the desired clopidogrel from the resolved intermediate (see Reaction Scheme 1).

Reaction Scheme 1

European Patent No. 0,281,459

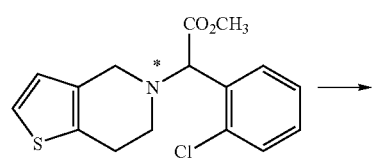

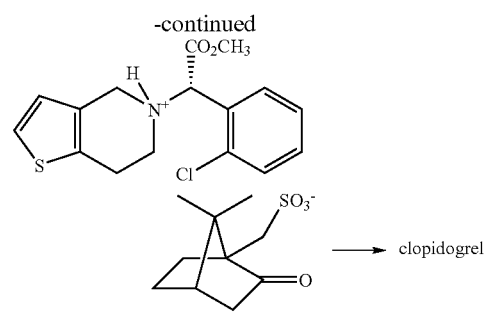

European Patent No. 0,099,802

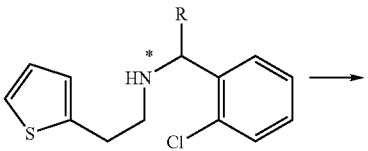

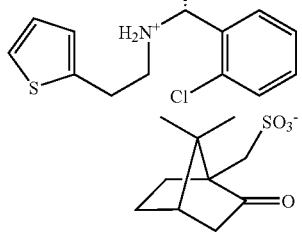

(R = CN, CONH₂)

European Patent No. 1,353,928

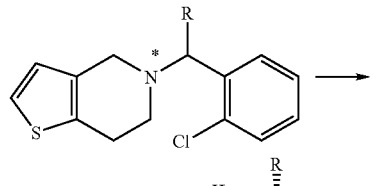

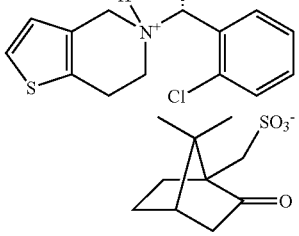

(R = CN, CONH₂)

However, these methods have the problem that the salt of clopidogrel or an intermediate thereof formed by the selective crystallization from the racemate of clopidogrel or its intermediate and (1R)-(−)-10-camphorsulfonic acid has an insufficient optical purity and must be subjected to further purification, the purification resulting in a yield reduction. In addition, it is difficult to recover (1R)-(−)-10-camphorsulfonic acid from the reaction solution for the purpose of recycling due to its high solubility in water.

SUMMARY OF THE INVENTION

Accordingly, it is a primary object of the present invention to provide a simple, high-yield method for preparing optically pure clopidogrel.

It is another object of the present invention to provide a novel intermediate used in the preparation of clopidogrel.

In accordance with one aspect of the present invention, there is provided a method of preparing clopidogrel of formula (I) comprising the steps of:

(a) optically resolving the racemic form of the compound of formula (II) using an optically active amine to form the optically active form of the compound of formula (III) or its acid-addition salt; and (b) methylating the compound of formula (III) or its acid-addition salt formed in step (a):

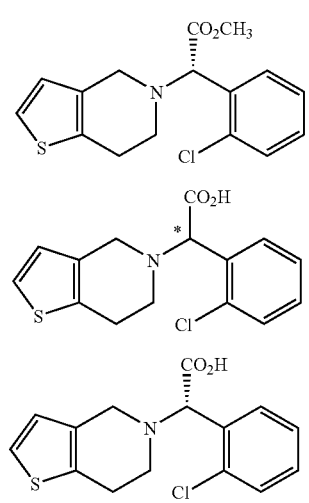

In accordance with another aspect of the present invention, there is provided a salt of formula (IV) used as an intermediate in the preparation of clopidogrel:

(IV)

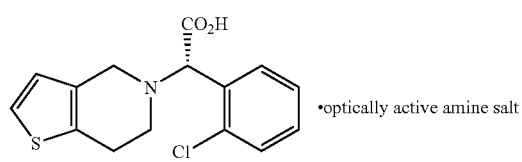

·optically active amine salt

DETAILED DESCRIPTION OF THE INVENTION

The method of the present invention comprises an optical resolution process (step (a) composed of sub-steps (a-1) and (a-2)) and an esterification process (step (b)), as shown in Reaction Scheme 2.

Reaction Scheme 2

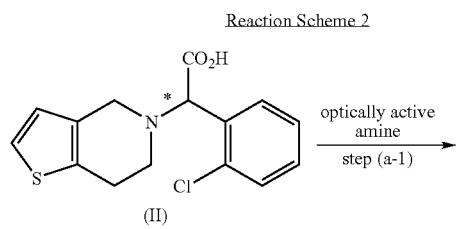

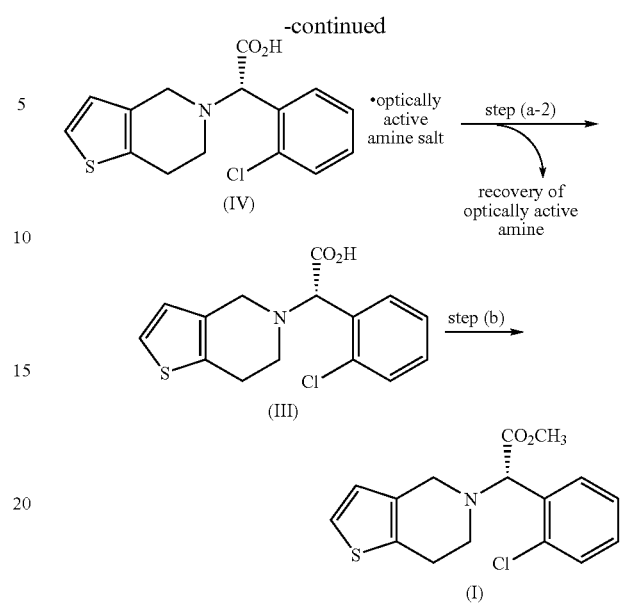

<Step (a)>

The optical resolution process (step (a)) in accordance with the present invention comprises reacting the racemic form of the compound of formula (II) with an optically active amine to crystallize a salt of formula (IV) (step (a-1)) and removing the optically active amine moiety from the salt to form the optically active form of the compound of formula (III) (step (a-2)).

<Step (a-1)>

The crystallization of the salt of formula (IV) in step (a-1) may be performed by adding the compound of formula (II) and the optically active amine into a suitable solvent, stirring the resulting solution at a temperature ranging from room temperature to the boiling point of the solvent and allowing the resulting mixture to cool to 0° C. to room temperature.

The optically active amine used in the present invention may be one of any conventional optical resolution agents used for optical resolution of a racemic carboxylic acid (see [E. L. Eliel, S. L. Eliel and L. N. Mander, *Stereochemistry of Organic Chemistry*, 1994, John Wiley & Son, New York, pp 329-337]). Such an amine is selected from the group consisting of ephedrine, 2-amino-1,2-diphenylethanol, α-methylbenzylamine, α-(1-naphtyl)ethylamine, glucamine, 2-amino-1-phenyl-1,3-propandiol and derivatives thereof, preferably, a (1R,2R)-(−)-2-amino-1-(4-substituted phenyl)-1,3-propandiol compound of formula (V):

(V)

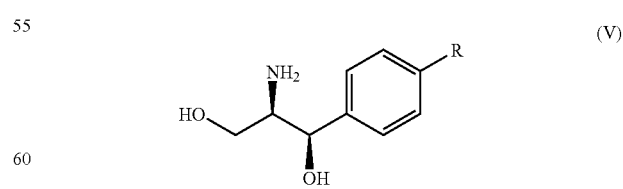

wherein, R is hydrogen, halogen, nitro, methyl or methoxy.

The optically active amine may be used in an amount ranging from 0.4 to 1.1 mole equivalents based on the amount of the compound of formula (II).

Suitable for use as the solvent in the present invention is an organic solvent such as methanol, ethanol, isopropanol, acetone, ethyl acetate, acetonitrile, tetrahydrofuran, 1,4-dioxane and N,N-dimethylformamide, or a mixture of one of the organic solvents and water.

The salt of formula (IV) thus obtained has a satisfactory optical purity, which does not require further purification, but, if necessary, it may be further recrystallized from any of the solvents listed above to improve the purity thereof.

<Step (a-2)>

In step (a-2), the compound of formula (III) may be prepared by alkalinizing the aqueous solution of the salt of formula (IV) with a base, followed by filtration or extraction, to separate the optically active amine from the salt of formula (IV) for further recycling, and acidifying the filtrate, which is extracted with an organic solvent.

The base used in the present invention may be sodium hydroxide or potassium hydroxide, and its amount is preferably in the range of 1 to 3 mole equivalents based on the amount of the compound of formula (IV).

The isolation of the optically active amine liberated from the salt is achieved through filtration; and when it is a liquid, it can be isolated by extraction using a conventional organic solvent. The optically active amine thus isolated may be reused in the crystallization process of step (a-1) via a simple purification procedure including a recrystallization or distillation step.

After the removal of the optically active amine moiety, the filtrate is acidified such that its pH becomes to 2 to 5, which is then extracted with an organic solvent such as ethyl acetate, chloroform and dichloromethane. The resulting extract is concentrated to give the compound of formula (III) in the form of a foam. Preferably, the compound of formula (III) thus obtained is converted to the form of pure acid-addition salt crystals, e.g., hydrochloride crystals.

The racemic form of the compound of formula (II) may be prepared by a conventional method (see European Patent No. 0,099,802). Preferably used in the inventive method are 4,5,6,7-dihydro-4H-thieno[3,2-c]pyridine or its acid-addition salt and α-bromo-(2-chlorophenyl)acetic acid which both are commercially available, as shown in Reaction Scheme 3.

Reaction Scheme 3

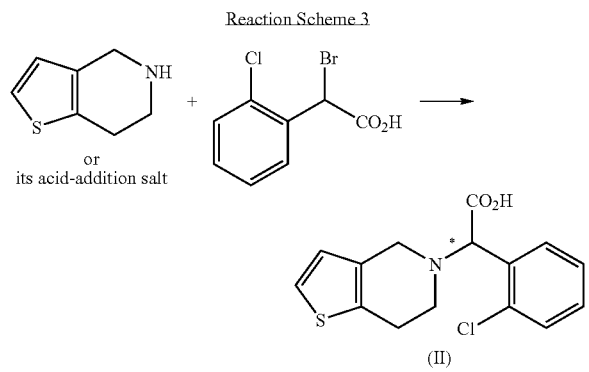

Specifically, the compound of formula (II) may be prepared by reacting α-bromo-(2-chlorophenyl)acetic acid with 4,5,6,7-dihydro-4H-thieno[3,2-c]pyridine or its acid-addition salt in a suitable solvent in the presence of a base.

Representative examples of the solvent which may be used in the present invention include water, methanol, ethanol, n-propanol, isopropanol, acetone, tetrahydrofuran, 1,4-dioxane, acetonitrile and a mixture thereof, and representative examples of the base used in the present invention, sodium hydroxide, potassium hydroxide, sodium carbonate, potassium carbonate and a mixture thereof. Based on the amount of 4,5,6,7-dihydro-4H-thieno[3,2-c]pyridine or its acid-addition salt, the amount of the base used is in the range of 1 to 10 mole equivalents, preferably of 2 to 4 mole equivalents, and the amount of the α-bromo-(2-chlorophenyl)acetic acid, in the range of 0.5 to 2 mole equivalents, preferably of 0.9 to 1.1 mole equivalents. This reaction may be conducted at a temperature ranging from 0° C. to the boiling point of the solvent, preferably from 5 to 40° C.

<Step (b)>

The methylation step (b) may be performed by: (i) reacting the compound of formula (III) or its acid-addition salt with a chlorinating agent in an inert solvent to form a chlorinated compound of formula (VI) or its acid-addition salt, which is treated with methanol; or (ii) reacting the compound of formula (III) or its acid-addition salt with an alkyl chloroformate in an inert solvent in the presence of a base to form an acid-anhydride of formula (VII), which is treated with methanol; or (iii) reacting the compound of formula (III) or its acid-addition salt with methanol in the presence of an acid catalyst:

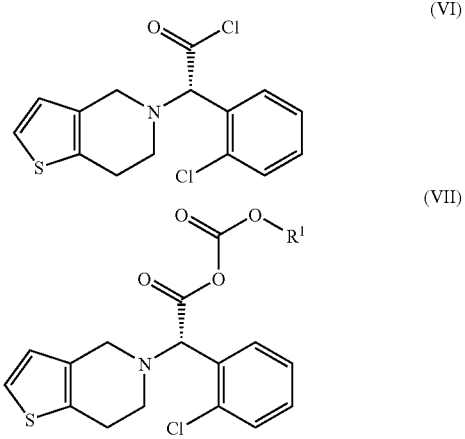

wherein, $R^1$ is $C_{1-4}$ alkyl.

In step (b), the reaction of the compound of formula (III) or its acid-addition salt with a chlorinating agent may be conducted in an inert solvent such as dichloromethane, chloroform, benzene and toluene at a temperature ranging from −30 to 40° C., preferably from −15° C. to room temperature, to achieve the formation of the chlorinated compound of formula (VI) or its acid-addition salt. Representative examples of the chlorinating agent used in the present invention include thionyl chloride, phosphorus pentachloride, phosphoryl chloride, phosgene, diphosgene, triphosgene, oxalyl chloride and a mixture thereof, wherein oxalyl chloride is preferred. The amount of the chlorinating agent used is preferably in the range of 1 to 5 mole equivalents based on the amount of the compound of formula (III) or its acid-addition salt.

Then, the reaction of the chlorinated compound of formula (VI) or its acid-addition salt with methanol may be performed at a temperature ranging from −15° C. to room temperature. The amount of methanol used is preferably in the range of 1 to 10 mole equivalents based on the amount of the compound of formula (III) or its acid-addition salt.

The reaction of the compound of formula (III) or its acid-addition salt with an alkyl chloroformate may be conducted in an inert solvent such as dichloromethane, chloroform, tetrahydrofuran, acetonitrile, benzene and toluene in the presence of a base at a temperature ranging from −30 to 40° C., preferably from −15° C. to room temperature, to obtain the acid-anhydride of formula (VII). Suitable for use in this step is alkyl chloroformate such as methyl chloroformate, ethyl chloroformate, n-propyl chloroformate, isopropyl chloroformate and isobutyl chloroformate. Representative examples of the base used in said step include triethylamine, diisopropyl ethylamine, tributylamine, pyridine, picoline, rutidine, dimethylaminopyridine and a mixture thereof. The amounts of the alkyl chloroformate and base are preferably in the range of 1 to 3 mole equivalents and of 1 to 4 mole equivalents, respectively, based on the amount of the compound of formula (III) or its acid-addition salt.

The reaction of the acid-anhydride of formula (VII) with methanol may be performed by adding methanol to the mixture obtained in the above step and stirring the resulting mixture at a temperature ranging from −15° C. to room temperature. The amount of methanol used is preferably in the range of 1 to 10 mole equivalents based on the amount of the compound of formula (III) or its acid-addition salt.

The reaction of the compound of formula (III) or its acid-addition salt with methanol may be conducted in methanol in the presence of an acid catalyst such as anhydrous hydrochloric acid, sulfuric acid, methanesulfonic acid and p-toluenesulfonic acid. The amount of the acid catalyst used is preferably in the range of 1 to 4 mole equivalents based on the amount of the compound of formula (III) or its acid-addition salt. Preferably, this reaction is performed at the boiling point of methanol used as a solvent.

The optically active methyl ester of clopidogrel of formula (I) thus obtained is practically free of the levorotatory isomer and it may be converted to its acid-addition salt form by a conventional method (see European Patent No. 0,281,459 and International Application Patent No. PCT/KR2004/002665). Such salts of clopidogrel include hydrochloride, hydrogen bromide, hydrogen sulfate, benzenesulfonate, 2-naphthalene sulfonate and 1,5-naphthalene disulfonate salts.

Clopidogrel or its acid-addition salt obtained in accordance with the inventive method has a high optical purity of at least 98% ee, which meets the minimum pharmaceutical purity required by US Pharmacopoeia.

Further, the salt of formula (IV) used as an intermediate in the preparation of clopidogrel according to the present invention is a novel compound containing an optically active amine such as ephedrine, 2-amino-1,2-diphenylethanol, α-methylbenzylamine, α-(1-naphtyl)ethylamine, glucamine, 2-amino-1-phenyl-1,3-propandiol and derivatives thereof, preferably that of (1R,2R)-(−)-2-amino-1-(4-substituted phenyl)-1,3-propanediol of formula (V).

The following Examples are given for the purpose of illustration only, and are not intended to limit the scope of the invention.

Example 1

Preparation of (±)-α-(2-chlorophenyl)-6,7-dihydro-4H-thieno[3,2-c]pyridine-5-acetic acid (formula (II))

50.0 g of 4,5,6,7-tetrahydrothieno[3,2-c]pyridine hydrochloride and 74.6 g of α-bromo-(2-chlorophenyl)acetic acid were successively added to a mixture of 275 ml of water and 75 ml of methanol, and the resulting solution was cooled to below 10° C. while stirring. 63.9 g of 85.0% KOH dissolved in 142 ml of water was slowly added to the above solution while maintaining the temperature at below 15° C. The resulting transparent solution was heated to 40° C. and stirred at that temperature for 3 hrs. The pH of the reaction solution was adjusted to 3.5 with 6N-HCl, cooled to room temperature and stirred for 2 hrs. Then, the reaction mixture was further cooled to below 5° C. and stirred for 2 hrs. The precipitated crystals were filtered, washed sequentially with 150 ml of water and 100 ml of n-hexane, and dried at 40° C. to obtain 81.7 g of the title compound (yield: 88%) as a white-yellow monohydrate.

m.p.: 114-116° C.

water content: 5.6% (Kahl-Fisher method)

$^1$H-NMR (CDCl$_3$, ppm): δ 3.00 (brs, 2H), 3.16-3.56 (m, 2H), 4.05-4.28 (m, 2H), 5.14 (d, 1H, J=4.4 Hz), 6.04 (brs, H), 6.55-6.68 (m, 1H), 7.04 7.31 (m, 1H), 7.31-7.41 (m, 1H), 7.85-7.98 (m, 1H)

$^{13}$C-NMR (CDCl$_3$, ppm): δ 22.64, 48.47, 50.43, 67.13, 124.72, 125.58, 128.00, 129.35, 130.36, 130.57, 130.72, 132.01, 132.06, 135.63, 170.34

IR (KBr, cm$^{-1}$): 3394, 3079, 1668, 1638

MS (ESI, M/Z): 308.2 (M+H)

Example 2

Preparation of (S)-(+)-α-(2-chlorophenyl)-6,7-dihydro-4H-thieno[3,2-c]pyridine-5-acetic acid.(1R,2R)-(−)-2-amino-1-(4-nitrophenyl)-1,3-propanediol salt (formula (IV))

167.0 g of the (±)-α-(2-chlorophenyl)-6,7-dihydro-4H-thieno[3,2-c]pyridine-5-acetic acid monohydrate obtained in Example 1 and 55.0 g of (1R,2R)-(−)-2-amino-1-(4-nitrophenyl)-1,3-propanediol (formula (V): R is nitro) were added to a mixture of 1000 ml of water and 1500 ml of methanol, and the resulting solution was refluxed for 12 hrs. The resulting reaction mixture was slowly cooled to below 5° C. and stirred for 2 hrs. The precipitated crystals were filtered, washed with 200 ml of methanol and dried at 40° C. to obtain 113 g of the title compound (yield: 85% of the calculated value) as a white-yellow powder.

m.p.: 199-201° C.

optical rotation: $[α]_D^{20}$+9.53° (c=1%, DMF)

optical purity: 99.0% ee (HPLC, on the compound of formula (III))

$^1$H-NMR (DMSO-d$^6$, ppm): δ 2.61-2.91 (m, 4H), 2.92-3.07 (m, 1H), 3.12-3.28 (m, 1H), 3.35-3.45 (m, 1H), 3.52 (d, 1H, J=14.5 Hz), 3.68 (d, 1H, J=14.5 Hz), 4.50 (s, 1H), 4.79 (d, 1H, J=7.0 Hz), 6.74 (d, 1H, J=5.1 Hz), 7.10-7.35 (m, 3H), 7.39 (d, 1H, J=7.4 Hz), 7.63 (d, 2H, J=8.6 Hz), 7.74 (d, 1H, J=7.4 Hz), 8.21 (d, 2H, J=8.6 Hz)

$^{13}$C-NMR (DMSO-d$^6$, ppm): δ 25.29, 47.95, 50.34, 58.19, 59.38, 70.13, 70.57, 122.75, 123.27, 125.50, 126.74, 128.09, 128.34, 128.91, 130.41, 132.78, 133.76, 134.33, 137.45, 146.89, 150.15, 173.77

IR (KBr, cm$^{-1}$) 3419, 1920, 1606, 1556, 1518, 1350

40.0 g of the compound thus obtained was recrystallized from 280 ml of 90% isopropanol to obtain 35.0 g of the title compound having a higher purity.

m.p.: 207-208° C.

optical rotation: $[α]_D^{20}$+9.56° (c=1%, DMF)

optical purity: 99.9% ee (HPLC, on the compound of formula (III))

Example 3

Preparation of (S)-(+)-α-(2-chlorophenyl)-6,7-dihydro-4H-thieno[3,2-c]pyridine-5-acetic acid.(1R,2R)-(−)-2-amino-1-(4-nitrophenyl)-1,3-propanediol salt (formula (IV))

130.0 g of the (±)-α-(2-chlorophenyl)-6,7-dihydro-4H-thieno[3,2-c]pyridine-5-acetic acid monohydrate obtained in Example 1 and 42.4 g of (1R,2R)-(−)-2-amino-1-(4-nitrophenyl)-1,3-propanediol (formula (V): R is nitro) were added to a mixture of 800 ml of water and 3200 ml of isopropanol. Then, the resulting suspension was refluxed until it became a homogeneous solution. The resulting solution was cooled to below 5° C. and stirred for 2 hrs. The precipitated crystals were filtered, washed with 200 ml of isopropanol and dried at 40° C. to obtain 78.0 g of the title compound as a white-yellow solid (yield: 75% of the calculated value). This solid was identical to that obtained in Example 2.

m.p.: 201-202° C.
optical rotation: $[\alpha]_D^{20}$ +9.50° (c=1%, DMF)
optical purity: 99.4% ee (HPLC, on the compound of formula (III))

Example 4

Preparation of (S)-(+)-α-(2-chlorophenyl)-6,7-dihydro-4H-thieno[3,2-c]pyridine-5-acetic acid.(1R,2R)-(−)-2-amino-1-phenyl-1,3-propanediol salt (formula (IV))

10.0 g of the (±)-α-(2-chlorophenyl)-6,7-dihydro-4H-thieno[3,2-c]pyridine-5-acetic acid monohydrate obtained in Example 1 and 2.8 g of (1R,2R)-(−)-2-amino-1-phenyl-1,3-propanediol (formula (V): R is hydrogen) were added to 100 ml of 95% isopropanol. Then, the suspension was refluxed until it became a homogeneous solution. The resulting solution was cooled to below 5° C. and stirred for 2 hrs. The precipitated crystals were filtered, washed with 10 ml of isopropanol and dried at 40° C. to obtain 4.2 g of the title compound as a white-yellow solid (yield: 57% of the calculated value).

m.p.: 181-183° C.
optical purity: 99.0% ee (HPLC, on the compound of formula (III))
$^1$H-NMR (DMSO-d$^6$, ppm): δ 2.72-2.84 (4H, m), 2.99-3.03 (1H, m), 3.18 (1H, dd, J=11.51, 5.76 Hz.), 3.34 (1H, dd, J=11.63, 3.47 Hz.), 3.60 (2H, dd, J=49.87, 14.40 Hz.), 4.48 (1H, s), 4.58 (1H, d, J=8.37 Hz.), 6.74 (1H, d, J=5.09 Hz.), 7.22-7.41 (9H, m), 7.75 (1H, dd, J=7.54, 1.89 Hz.)
$^{13}$C-NMR (DMSO-d$^6$, ppm): δ 25.32, 47.96, 50.35, 58.57, 59.01, 70.83, 70.91, 122.70, 125.49, 126.67, 126.81, 127.57, 128.17, 128.83, 130.45, 132.77, 133.74, 134.42, 137.74, 142.18, 173.90
IR (KBr, cm$^{-1}$): 3455, 3069, 1561

Example 5

Preparation of (S)-(+)-α-(2-chlorophenyl)-6,7-dihydro-4H-thieno[3,2-c]pyridine-5-acetic acid (formula (III))

113.0 g of the salt obtained in Example 2 or 3 was added to 250 ml of water and cooled to below 5° C. 17.4 g of sodium hydroxide dissolved in 125 ml of distilled water was added thereto and stirred at that temperature for 30 min. The resulting precipitated crystals were filtered and washed with 125 ml of distilled water. 43.0 g of (1R,2R)-(−)-2-amino-1-(4-nitrophenyl)-1,3-propanediol (formula (V): R is nitro) was separated and recovered therefrom (recovery ratio: 93%). To the filtrate, on the other hand, 113 g of sodium chloride and 340 ml of chloroform were added, the pH of the resulting mixture was adjusted to 3.5 with 6N-HCl, and the organic layer was separated. The aqueous layer was further extracted with 340 ml of chloroform. The chloroform layers were combined, concentrated under a reduced pressure, to obtain 68 g of the title compound in the form of a foaming material.

optical purity: 99.0% ee (HPLC)

Example 6

Preparation of (S)-(+)-α-(2-chlorophenyl)-6,7-dihydro-4H-thieno[3,2-c]pyridine-5-acetic acid hydrochloride (hydrochloride of formula (III))

61 g of (S)-(+)-α-(2-chlorophenyl)-6,7-dihydro-4H-thieno[3,2-c]pyridine-5-acetic acid obtained in Example 5 was added to a mixture of 300 ml of acetone and 15 ml of methanol, and then heated to 40° C. 16.4 ml of concentrated hydrochloric acid was added thereto, and the resulting mixture was stirred at room temperature for 2 hrs, and then, at below 5° C. for at least 2 hrs. The precipitated crystals were filtered, washed with 100 ml of acetone and dried at 40° C. under a reduced pressure, to obtain 61 g of the title compound as a white-yellow solid (yield: 90%).

m.p.: 200-201° C.
optical rotation: $[\alpha]_D^{20}$ +64.87° (c=1%, MeOH)
optical purity: 99.5% ee (HPLC)
$^1$H-NMR (DMSO-d$^6$, ppm): δ 3.10 (s, 3H), 3.47 (s, 2H), 4.30 (s, 2H), 5.54 (s, 1H), 6.91 (d, 1H, J=4.8 Hz), 7.44 (d, 1H, J=4.8 Hz), 7.46-7.58 (m, 2H), 7.65 (d, 1H, 7.4 Hz), 7.97 (d, 1H, J=7.1 Hz)
$^{13}$C-NMR (DMSO-d$^6$, ppm): δ 21.78, 48.81, 50.17, 65.43, 125.04, 125.54, 127.99, 128.29, 128.36, 130.37, 130.46, 131.49, 132.02, 134.43, 167.53
IR (KBr, cm$^{-1}$): 3435, 3114, 1728

Example 7

Preparation of methyl (S)-(+)-α-(2-chlorophenyl)-6,7-dihydrothieno[3,2-a]pyridine-5(4H)-acetate (formula (I))

8.9 g of (S)-(+)-α-(2-chlorophenyl)-6,7-dihydro-4H-thieno[3,2-c]pyridine-5(4H)-acetic acid obtained in Example 5 was dissolved in 150 ml of anhydrous methanol, and 6.4 ml of anhydrous sulfuric acid was added thereto. The resulting mixture was refluxed for 24 hrs. The resulting mixture was then subjected to a reduced pressure to remove methanol therefrom. 200 ml of ethyl acetate and 150 ml of water were added to the resulting residue, the pH was adjusted to 8 using saturated sodium bicarbonate to induce phase separation. The organic layer was separated, dried over anhydrous magnesium sulfate and concentrated under a reduced pressure, to obtain 7.2 g of the title compound as a yellow oil (yield: 77%).

optical purity: 98.5% ee (HPLC)
$^1$H-NMR (DMSO-d$^6$, ppm): δ 2.89 (s, 4H), 3.60-3.78 (m, 2H), 3.73 (s, 3H), 4.93 (s, 1H), 6.67 (d, 1H, J=5.1 Hz), 7.06 (d, 1H, J=5.1 Hz), 7.26-7.30 (m, 2H), 7.37-7.45 (m, 1H), 7.68-7.77 (m, 1H)

Example 8

Preparation of methyl (S)-(+)-α-(2-chlorophenyl)-6,7-dihydrothieno[3,2-a]pyridine-5(4H)-acetate (formula (I))

8.9 g of (S)-(+)-α-(2-chlorophenyl)-6,7-dihydro-4H-thieno[3,2-c]pyridine-5(4H)-acetic acid obtained in Example 5 was dissolved in 150 ml of anhydrous methanol, and 7.5 ml of methanesulfonic acid was added thereto. The resulting mixture was then refluxed for 24 hrs, and subjected to a reduced pressure to remove methanol therefrom. 200 ml of ethyl acetate and 150 ml of water were added to the resulting residue, the pH was adjusted to 8 using saturated sodium bicarbonate to induce phase separation. The organic layer was separated, dried over anhydrous magnesium sulfate and concentrated under a reduced pressure, to obtain 6.1 g of the title compound as a yellow oil (yield: 65%), identical to that obtained in Example 7.

optical purity: 98.5% ee (HPLC)

Example 9

Preparation of methyl (S)-(+)-α-(2-chlorophenyl)-6,7-dihydrothieno[3,2-a]pyridine-5(4H)-acetate (formula (I))

8.9 g of (S)-(+)-α-(2-chlorophenyl)-6,7-dihydro-4H-thieno[3,2-c]pyridine-5(4H)-acetic acid obtained in Example 5 was dissolved in 60 ml of dichloromethane, 0.2 ml of dimethylformamide was added thereto and the resulting mixture was cooled to −20° C. A mixture of 4.7 ml of oxalyl chloride and 20 ml of dichloromethane was slowly added thereto at below −10° C. over a period of 30 min, and then stirred at a temperature of −10 to 0° C. for 2 hrs. A mixture of 5.4 ml of methanol and 20 ml of dichloromethane was then added to the above mixture over a period of 30 min, slowly heated to room temperature and then stirred at the same temperature for 2 hrs. 70 ml of water was slowly added to the resulting solution, the pH was adjusted to 7.5 using saturated sodium bicarbonate to induce phase separation. The organic layer was separated, washed with 150 ml of saturated sodium chloride, dried over anhydrous magnesium sulfate and concentrated under a reduced pressure, to obtain 8.9 g of the title compound as a yellow oil (yield: 96%), identical to that obtained in Example 7.

optical purity: 98.1% ee (HPLC)

Example 10

Preparation of methyl (S)-(+)-α-(2-chlorophenyl)-6,7-dihydrothieno[3,2-a]pyridine-5(4H)-acetate (formula (I))

41.8 g of (S)-(+)-α-(2-chlorophenyl)-6,7-dihydro-4H-thieno[3,2-c]pyridine-5(4H)-acetic acid hydrochloride obtained in Example 6 was suspended in 252 ml of dichloromethane, 0.94 ml of dimethylformamide was added thereto and cooled to −20° C. A mixture of 12.8 ml of oxalyl chloride and 84 ml of dichloromethane was slowly added thereto at below −10° C. over a period of 30 min, and then stirred at a temperature in the range of −10 to 0° C. for 2 hrs. A mixture of 24.6 ml of methanol and 84 ml of dichloromethane was added thereto over a period of 30 min, the resulting mixture was heated to room temperature and then stirred at the same temperature for 2 hrs. 170 ml of water was slowly added to the resulting solution, the pH was adjusted to 7.5 using saturated sodium bicarbonate to induce phase separation. The resulting organic layer was separated, washed with 150 ml of saturated sodium chloride, dried over anhydrous magnesium sulfate and concentrated under a reduced pressure, to obtain 37.1 g of the title compound as a yellow oil (yield: 95%), which was identical to that obtained in Example 7.

optical purity: 98.5% ee (HPLC)

Example 11

Preparation of methyl (S)-(+)-α-(o-chlorophenyl)-6,7-dihydrothieno[3,2-a]pyridine-5(4H)-acetate (formula (I))

7.9 g of (S)-(+)-α-(2-chlorophenyl)-6,7-dihydro-4H-thieno[3,2-c]pyridine-5(4H)-acetic acid obtained in Example 5 was dissolved in 80 ml of dichloromethane, 5 ml of triethylamine was added thereto and the resulting mixture was cooled to below −10° C. 2.6 ml of methyl chloroformate was added thereto and stirred at 0° C. for 2 hrs. Then, 4 ml of methanol was added to the resulting mixture, 1.6 g of 4-dimethylaminopyridine was added thereto, and the resulting mixture was stirred at that temperature for 1 hr and further stirred at room temperature for 1 hr. The reaction mixture was then washed sequentially with saturated ammonium chloride and sodium bicarbonate. The resulting organic layer was separated, dried over anhydrous magnesium sulfate and concentrated under a reduced pressure, to obtain 6.0 g of the title compound as a yellow oil (yield: 73%), which was identical to that obtained in Example 7.

optical purity: 98.0% ee (HPLC)

Reference Example 1

Preparation of Chlopidogrel Hydrogen Sulfate (Hydrogen Sulfate of Formula (I))

According to the method disclosed in European Patent No. 0,281,459, 35.0 g of chlopidogrel obtained in Example 9 was dissolved in 150 ml of acetone, and 12.5 g of concentrated sulfuric acid was added thereto. The resulting mixture was cooled to below 10° C. and stirred overnight. The precipitated crystals were filtered, washed with acetone and dried, to obtain 39.7 g of the title compound (yield: 87%).

optical purity: 98.5% ee (HPLC)

Reference Example 2

Preparation of Chlopidogrel 1,5-naphthalene Disulfonate (1,5-naphthalenedisulfonate of Formula (I))

According to the method disclosed in International Application Patent No. PCT/KR2004/002665, 35.0 g of chlopidogrel obtained in Example 9 was dissolved in 200 ml of acetone. 20.2 g of 1,5-naphthalenedisulfonic acid tetrahydrate dissolved in a mixture of 140 ml of acetone and 10 ml of water was added to the chlopidogrel solution over a period of 30 min, and the resulting mixture was stirred at room temperature for 12 hrs, and then 0 to 5° C. for 4 hrs. The precipitated crystals were filtered, washed with 100 ml of cold acetone and dried at 50° C. to obtain 46.7 g of the title compound crystals as a white powder (yield: 90%).

m.p.: 223-225° C.

water content: 1.91% (Kahl-Fisher method)

optical purity: 99.8% ee (HPLC)

As shown above, the method of the present invention gives optically pure clopidogrel in a high yield.

While the invention has been described with respect to the above specific embodiments, it should be recognized that various modifications and changes may be made to the invention by those skilled in the art which also fall within the scope of the invention as defined by the appended claims.

What is claimed is:

1. An optically active amine salt of the compound (III):

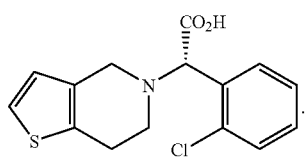

(III)

2. The optically active amine salt of claim 1, wherein the optically active amine is selected from the group consisting of ephedrine, 2-amino-1,2-diphenylethanol, α-methylbenzylamine, α-(1-naphtyl)ethylamine, glucamine, 2-amino-1-phenyl-1,3-propandiol and derivatives thereof.

3. The optically active amine salt of claim 1, wherein the optically active amine is a compound of formula (V):

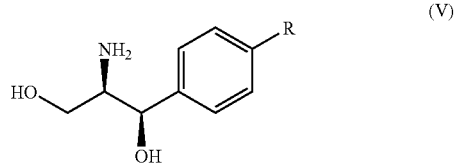

(V)

wherein, R is hydrogen, halogen, nitro, methyl or methoxy.

4. The optically active amine salt of claim 3, wherein R is hydrogen or nitro.

* * * * *